United States Patent [19]

Brown et al.

[11] 4,064,227

[45] Dec. 20, 1977

[54] RADIOIMMUNOASSAY METHOD FOR THE DETERMINATION OF CARDIOTONIC GLYCOSIDES

[75] Inventors: James L. Brown, House Springs; Leo R. Lyle, Webster Groves, both of Mo.

[73] Assignee: Mallinckrodt, Inc., St. Louis, Mo.

[21] Appl. No.: 558,756

[22] Filed: Mar. 17, 1975

[51] Int. Cl.$^2$ .................... G01N 33/00; G21H 5/02
[52] U.S. Cl. .................................. 424/1; 23/230 B
[58] Field of Search .................... 23/230 B, 230.6; 424/1.5, 1; 260/239.57

[56] References Cited

U.S. PATENT DOCUMENTS

| | | | |
|---|---|---|---|
| 3,666,854 | 5/1972 | Eisentraut | 424/1 |
| 3,799,740 | 3/1974 | Mincey | 23/230 B |
| 3,810,886 | 5/1974 | Rutner et al. | 260/239.57 |
| 3,855,208 | 12/1974 | Rutner et al. | 260/239.57 |
| 3,925,355 | 12/1975 | Piasio et al. | 424/1 X |

OTHER PUBLICATIONS

Lanoxitest γ, Wellcome Reagents Ltd., Nov. 1973, pp. 1-6.
Oliver, Jr. et al, The Journal of Clinical Investigation, vol. 47, 1968, pp. 1035-1042.
Sterling et al, Journal of Clinical Endocrinology and Metabolism, vol. 21, Apr. 1961, pp. 456-464.

*Primary Examiner*—Benjamin R. Padgett
*Assistant Examiner*—Christine M. Nucker
*Attorney, Agent, or Firm*—R. J. Klostermann

[57] ABSTRACT

An improved, simplified radioimmunoassay method for the in vitro determination of cardiotonic glycosides in unextracted blood serum involves the use of a reagent constituting a buffer solution containing a radioactive hapten for such glycosides. Packaged test kits for use in conveniently carrying out the radioimmunoassay are also provided.

6 Claims, No Drawings

RADIOIMMUNOASSAY METHOD FOR THE DETERMINATION OF CARDIOTONIC GLYCOSIDES

BACKGROUND OF THE INVENTION

This invention relates to radioimmunoassay methods and, more particularly to radioimmunoassay methods, reagents and packaged test kits for the in vitro determination of cardiotonic glycosides in unextracted blood serum.

DESCRIPTION OF THE PRIOR ART

Radioimmunoassay methods for measuring digitoxin are known. For example, they are described in U.S. Pat. Nos. 3,855,208 and 3,810,886 and German publication Pat. No. 2,331,922.

While certain known radioimmunoassay methods for determining digitoxin or digoxin in blood serum may be suitable for clinical use, their usefulness is somewhat limited because such methods are time consuming and/or require a large number of procedural operations on the part of the technician which may introduce errors and affect the accuracy or reproducibility of the assay results. Thus the commercially available test kits for use in carrying outt digoxin or digitoxin radioimmunoassay determinations typically contain a plurality of reagents and their clinical use requires the technician to perform many time consuming operations in preparing the reagents andor conducting the radioimmunoassay.

Consequently, a method for determining digitoxin and digoxin in unextracted blood serum which may be conducted relatively rapidly and with fewer procedural operations being required on the part of the technician conducting the assay and which does not affect the sensitivity, accuracy or reproducibility of the assay results would be an advancement in the art.

SUMMARY OF THE INVENTION

Briefly the invention is directed to a radioimmunoassay method for the in vitro determination of a cardiotonic glycoside such as digitoxin or digoxin in unextracted blood serum which comprises the steps of mixing a sample of blood serum whose cardiotonic glycoside content is to be determined with a reagent comprising an aqueous buffer solution containing a radioactive hapten for such glycoside, adding to the mixture an antiserum containing antibody capable of immunoreactivity with such glycoside and such hapten, incubating the resultant mixture at a tempeature and for a sufficient period of time to produce substantial equilibration of the antibody bound hapten and cardiotonic glycoside, separating the unbound hapten from the antibody bound hapten, and determining the relative amounts of antibody bound radioactive hapten and unbound radioactive hapten.

The invention is further directed to a packaged test kit for use in such radioimmunoassay methods comprising the combinatoion of (a) a buffer solution containing a radioactive hapten for a cardiotonic glycoside; (b) an antiserum containing antibody capable of immunoreactivity with such hapten and such glycoside; and (c) a plurality of relatively thin strips of a membrane consisting essentially of ion-exchange resin.

DETAILED DESCRIPTION OF THE INVENTION

In one embodiment of the invention, the first step of the radioimmunoassay method involves mixing a sample of mormal human blood serum whose cardiotonic glycoside content is to be determined with a reagent. This reagent, in accordance with the invention, comprises an aqueous buffer solution containing a radioactive hapten for the cardiotonic glycoside. It has been found that buffer and radioactive hapten can be mixed in solution and retain their activity even upon storage in the frozen state for reasonably long periods of time (e.g., 3 months). The use of such a reagent advantageously eliminates several procedural steps on the part of the technician without adversely affecting the accuracy, sensitivity or reproducibility of the assay.

The reagent contains effective and known quantities of phosphate buffer solution, radioactive hapten for the cardiotonic glycoside and an organic solvent.

The term hapten as used herein means a substance that does not stimulate antibody formation but reacts selectivity in vitro with an antibody.

The radioactive hapten used in the practice of this invention is preferably radioiodinated 3-succinyl digoxigenin-L-tyrosine, 3-succinyl digitoxigenin-L-tyrosine, 3-adiply-digitoxigenin-L-tyrosine, 3-adipyl-digoxigenin-L-tyrosine, 3-carbodigoxigenin-glycly-L-tyrosine or 3-carbondigitoxin-glycyl-L-tyrosine. Iodine-125 is the radioisotope of choice but other isotopes may be used such as Iodine-131. Other radioiodinated haptens may be used in the practive of this invention such as those described in U.S. Pat. Nos. 3,855,208, U.S. Pat. No. 3,810,886 and German publication 2,331,922 in the name of the Wellcome Foundation filed June 11, 1973, and published Jan. 10, 1974, all of which are incorporated herein by reference.

The aqueous phosphate buffer soltuion is prepared using anhydrous dibasic potassium phosphate, monobasic sodium phosphate, and sodium chloride. Preferably the buffer solution has a pH of 7.3 to 7.5. Other buffers may be used in the practice of this invention as long as they give a pH of 7.3 to 7.5 such as tris buffer and veronal buffer.

One of the preferred haptens is first dissolved in an inert organic solvent and this mixture is then admixed with the phosphate buffer solution. Ethanol, methanol, or reagent alcohol which is 95% ethanol and 5% isopropanol is preferred but other solvents such as dimethyl formamide may be used as long as they are miscible with the phosphate buffer solution.

The hapten is present in an amount to provide 7 to 100 nCi units of radioactivity. Generally the solvent is present in the aqueous buffer solution in an amount of from 0.5 to 5%, preferably about 1 to 2% by volume, based on the total volume of the buffer.

After the unknown sample of blood serum has been mixed with the reagent, an antiserum diluted in phosphate buffer solution containing antibody capable of immunoreactivity with the cardiotonic glycoside and the reaioactive hapten is added to the resultant mixture. The antibody present has a specificity for the cardiotonic glycoside and the radioactive hapten. Thus, the quantity of radioactive hapten bound by a given quantity of antibody is decreased in the presence of unlabelld cardiotonic glycoside from the unknown blood serum sample, and the effect is directly related to the concentration of the unlabelled glycoside.

Methods known to the art may be employed for producing antisera containing antibody capable of immunoreactivity with the cardiotonic glycoside and the hapten for use in the present invention. For example, one is produced by subcutaneous immunization with digoxin HSA conjugate in complete Freunds adjuvant. The conjugate is prepared by periodate oxidation according to Butler and Chen, Biochem J. 33:133, 1970. Other conjugates with digoxin or digitoxin can be prepared using BSA, ovalbumin, serum albumin, KLH and various synthetic polymers.

For use in the radioimmunoassay methods of the invention, it is preferred that the antiserum be diluted to the extent that 30 to 80%, preferably 50 to 70%, of a tracer quantity of radioactive hapten (7 – 100 nCi) is bound.

Once the antiserum has been added to the mixture of the blood serum sample and the reagent described above, the resultant mixture is incubated at a temperature and for a sufficient period of time to produce substantial equilibration of the antibody bound hapten and unbound cardiotonic glycoside. During incubation, the antibody in the diluted antiserum forms an immune complex with the radioactive hapten and serum cardiotonic glycosie (or cardiotonic glycoside standard solutions). In the practice of this invention it is preferred that the incubation step be conducted at a temperature of about 18° to 30° C. preferably 20° to 24° C. for a period of approximately about 20 to 35 minutes, preferably 30 minutes, after which binding of the hapten by the antibody has been found to reach substantial equilibrium.

Upon completion of the incubation step, the unbound hapten is separated from the antibody bound hapten.

Separation is conveniently effected through contacting of the mixture with a relatively thin strip of a membrane consisting essentially of an ion-exchange resin for a period of approximately ½ to 1 hour at room temperature. The ion-exchange resin membranes which may be employed in the present invention are relatively thin stips, sheets or films of a solid hydrous gel consisting of an insoluble polymeric matrix to which are attached dissociable cationic or anionic groups, the gel being preferably reinforced with some suitable fibrous material. Many useful resin membranes of this kind are known, as for example those described in U.S. Pat. Nos. 2,730,768, 2,780,604, 2,800,445 and 2,860,097. For example, a commercially available anionselective resin useful in the present invention is that marketed under the trade designation "AR-111" (by Ionics, Inc. of Watertown, Massachusetts).

Upon addition of the resin strips of the test and standard or control vials, the vials are capped and the contents incubated as by rotating the vials for ½ to 1 hour at room temperature. The rotation time should be the same for the unknown and control samples. As the end of the incubation period, the resin strips are removed as by means of forceps and discarded.

The relative amounts of antibody bound radioactive hapten and unbound radioactive hapten are then determined. Preferably, this is accomplished by a determination of the radioactive hapten in each vial by means of a gamma counter. The count rate of vial components following removal of the resin strip reflects the serum concentration of cardiotonic glycoside. A precount determination of radioactivity in the vial is made at the outset of the test on a gamma counter. The percent of radioactive hapten which is antibody bound is then calculated as follows:

$$\frac{\text{Net CPM Postcount}}{\text{Net CPM Precount}} \times 100 = \% \text{ hapten I-125 Bound to Antibody}$$

With increasing quantities of nonradioactive cardiotonic glycoside (patient or standard), the percent radioactive hapten bound by the antibody decreases. Based upon this principle, a standard curve is prepared by plotting the percent radioactive hapten bound by each of a series of standard sera versus their respective cardiotonic glycosides concentration. The patient's total circulating serum cardiotonic glycoside concentration is then readily determined by comparing the percent radioactive hapten bound in the patient's serum sample to the standard curve.

For use in carrying out the radioimmunoassay methods of the invention, packaged test kits containing the necessary reagents and materials are provided. For the practice of the first embodiment described above, the essential components of the preferred packaged test kit include a buffered solution containing the radioactive hapten, a buffered solution containing an antiserum and a plurality of relatively thin strips of an ion-exchange resin membrane. It may also include a plurality of solutions of serum containing varying amounts of cardiotonic glycoside, preserved with agents such as $NaN_3$.

A particular advantage of the kits is that on fixed volume pipette may be used to carry out the radioimmunoassay which reduces the chance of error when different volumes must be transferred. Also the standards in serum tends to assure accuracy, sensitivity and reproducibility of the assay by providing a vehicle most closely resembling the patient sample The invention is further illustrated by the following:

PHOSPHATE BUFFER

A 0.15 phosphate buffer solution having a pH of 7.4 was prepared by adding anhydrous dibasic potassium phosphate (1.39 gm), monobasic sodium phosphate (0.24 gm) and sodium chloride (9.00 gm) to physiological saline (900 ml.) in a liter beaker. Hydrochloric acid (IN) was added dropwise until the pH reached 7.4 ± .05. The solution was transferred to a 1 liter volumetric flask, diluted to a final volume of 1 liter and stored at 4° C. to 10° C. This buffer was supplemented with 0.1% bovine serum albumin and 0.01% $NaN_3$ when used as a diluent for the anti serum.

PREPARATION OF HIGH SPECIFIC ACTIVITY HAPTENS

I-125-3-succinyl digitoxigenin-L-tyrosine a. Succinylation was accomplished using the method for digitoxigenin described by Oliver G. C., B. M. Parker, D. L. Bransfield and C. W. Parker J. Clin. Inv. 47:1035 (1968). 200.0 mgs digitoxigenin and 389.0 mgs succinic anhydride were dissolved in 6.1 ml pyridine. After 3 months at room temperature the reaction products were isolated and purified according to Oliver et al.

b. Tyrosination was accomplished using a temperatue controlled mixed anhydride reaction which favors the formation of a stable succinyl digitoxigenin complex with the α-amino groups of tyrosine. The reaction conditions favor the rapid degradation of excess isobutyl chloroformate so that minimal activation of carboxyl groups on tyrosine takes place.

10 mgs of succinyl digitoxigenin (0.021 mM) (a above) was dissolved with magnetic stirring in 0.5 ml of dimethyl formamide that had been chilled to −20° C. in a dry ice isobutyl alcohol bath. After 10 minutes 0.042 mM of isobutyl chloroformate is added and after two minutes 0.042 mM of tri-ethyl amine. The reaction mixture is held with constant stirring at −20° C. for two hous after which it is allowed to warm to 0° C. and is held at this temperature for 15 - 20 minutes. Twenty-five ul aliquots of this mixture are added to 2.0 ml distilled water containing 4.76 mg tyrosine HCl (0.021 mM) (pH has previously been adjusted to pH 9.0 with 1.0N NaOH). The pH is maintained at 9.0 throughout the course of addition with more 1.0N NaOH. After addition of the activated anhydride to the tyrosine, the mixture was held, with constant stirring, at 0° C. for 2 hours. It was then analyzed on CHROMAR (R) 7GF Thin Layer Chromatography Plates. The solvent system consisted of 90 parts of chloroform and 10 parts of methyl alcohol (anhydrous). Two compounds are detectable with ultraviolent light. One at the origin (tyrosine) and another at rf 0.3. Both give a reaction with ninhydrin.

The Rf 0.3 material is removed from the plate and dissolved in a small (0.1 ml) volume of methyl alcohol.

c. Iodination - 50 microliters of the above 3-O-succinyl digitoxigenin tyrosine in methyl alcohol are added to 100 ul of 0.5M phosphate buffer. Two mC of carrier free 21 99.9% radio purity Na$^{125}$I in 0.1N NaOH was added. After 30 seconds, 2.5 ul of 7 mg/ml solution of chloramine T in 0.25M phosphate buffer (a 1:2 dilution of 0.5M phosphate buffer listed above) was added. After 30 seconds, 2.5 of a 7 mg/ml solution of sodium metabisulfite in 0.25 M phosphate buffer was added. This reaction mixture was again chromatographed on CHROMAR (R) 7GF TLC plates in a chloroform-methanol (90:10) solvent system and found to have the same Rf (0.3) as the starting material. The material was eluted from the plates with 1 - 2 ml of 10 ul methyl alcohol and diluted in the same solvent to 1 - 12 uc per 10 ul for inclusion in the reaction vials (Specific activity 375 to 600 uCl/ug).

3-succinyl-digoxigenin-L-tyrosine I-125

This compound was prepared according to the following sequence and then labelled.

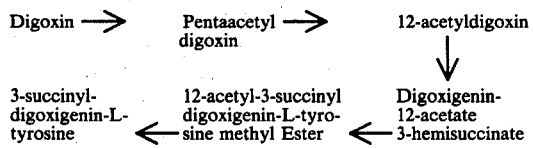

a. Pentaacetyl-digoxin This compound was prepared by the procedure of H. W. Voigtlander and G. Balsam, Arch. Pharm., 301, 208 (1968).

A mixture of 1.8 g of digoxin, 40 ml of acetic anhydride and 30 ml of pyridine was refluxed under a nitrogen atmosphere for 90 minutes. The solvent was removed under reduced pressure and the residue was dissolved in chloroform. The chloroform solution was washed successively with aqueous sodium bicarbonate and 0.1N hydrochloric acid, dried over magnesium sulfate, and evaporated to leave the crude product, mp 95°–116° C. No purification was done prior to subsequent reaction.

b. 12-Acetyldigoxigenin

The crude acetylated product obtained above was refluxed for 45 min. in a mixture of 150 ml of methanol and 150 ml of 0.1N sulfuric acid. After evaporating the methanol at R.T. under reduced pressure, the product was extracted with chloroform. The chloroform layer was washed with saturated aqueous sodium bicarbonate, water, dried (MgSO$_4$) and evaporated to leave a gummy residue which was recrystallized twice with acetone-pet. ether-ether to give 0.25 g of the desired product, mp 276°–280°.

c. Digoxigenin-12-acetate-3-hemisuccinate

A solution of 880 mg of 12-acetyldigoxigenin and 880 mg of succinic anhydride in 10 ml of pyridine was refluxed under a nitrogen atmosphere for 7.5 hours. About 10 ml of saturated aqueous sodium bicarbonate solution was added and the solvents were evaporated. The residue was dissolved in water, washed thoroughly with ethyl acetate, acidified with hydrochloric acid at 0° C., and extracted with three portions of ethyl acetate. The combined extracts were washed with brine, dried (MgSO$_4$) and evaporated to leave a residue which was purified by thin-layer chromatography (Rf. 18–0.36, acetone-hexane-pet. ether, 10:7:3) to give 540 mg (49.8% yield) of the desired product, mp 110°–120° C.

d. 12-Acetyl-3-succinyl-digoxigenin-L-tyrosine methyl ester

A mixture of 22.4 mg digoxigenin-12-acetate-3-hemisuccinate, 0.004 ml of triethylamine in 0.4 ml of dichloromethane and 0.00539 ml of pivaloyl chloride in 0.5 ml of dichloromethane was stirred at RT under nitrogen atmosphere for 15 min. and chilled to −10° C. prior to addition of a solution of 7.7 mg of L-tyrosine methyl ester in 0.2 ml pyridine. After stirring at −10° C. for 10 min. and at RT for 1 hr. the mixture was diluted with water, acidified with dil. HCl at 0° C. and extracted with dichloromethane. The extract was washed with aqueous sodium bicarbonate, water, dried (MgSO$_4$) and evaporated. A preparative silica gel tlc (acetone-pet. ether-hexane, 8:3:7) of the residue gave five bands at R$_f$ 0.521–0.490, 0.742–0.412, 0.290–0.242, 0.170–0.109 and 0.0909–0.0667. The desired product (gum, 5.3 mg, 17.8% yield, R$_f$0.170–0.109) was collected and identified by ir and UV.

e. 3-Succinyl-digoxigenin-L-tyrosine

A mixture of 546 mg of 12-acetyl-3-succinyl-digoxigenin-L-tyrosine methyl ester, 2,148 mg of potassium carbonate, 54.6 ml of methanol and 54.6 ml of water was allowed to stand at RT. After 3 hours, the methanol was evaporated at RT under reduced pressure, diluted with water, washed with several portions of ethyl acetate, acidified with dil. HCl at 0° C., and extracted with three portions of ethyl acetate. The combined extracts were washed with water, dried (MgSO$_4$), and evaporated. Purification of the residue by silica gel preparative tlc (Brinkmann, 2 mm thickness, R$_f$ = 0.10 - 0.17, CHCl$_3$:MeOH:AcOH - 16:2:1) afforded about 103 mg of pure product, melted at 145°–153°, decomposed at 165°–170°.

f. Iodination 2 mg of 3-succinyl-digoxigenin-L-tyrosine dissolved in 10 ml of reagent alcohol and 25 microliters of this soluti on are added to 100 ml of 0.5 phosphate buffer.

Two mCi of carrier free < 99.9% radio purity Na$^{125}$I in 0.1N NaOH was added. After 30 seconds, 2.5 ul of 7mg/ml solution of chloramine T in 0.25M phosphate buffer (a 1:2 dilution of 0.5M phosphate buffer listed above) was added. After 30 seconds, 2.5 ul of a 7 mg/ml solution of sodium metabisulfite in 0.25 M phosphate buffer was added. This reaction mixture was chromatographed on CHROMAR$^{(R)}$ 7GF TLC plates in a chloroform - methanol formate (90:10:0.5) solvent system and found to have the same Rf as the starting material. The material was eluted from the plates with 1 – 2 ml of 10 ul methyl alcohol and diluted in the same solvent to 1 – 12 uCi per 10 ul for inclusion in the reaction vials (Specific activity 375 to 600 uCi/ug).

3-adipyl-digoxigenin-L-tyrosine I-125

This compound was prepared according to the following sequence and then labelled.

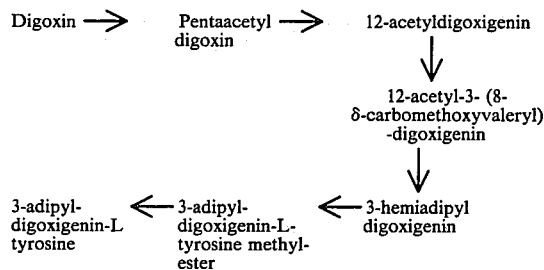

a. 12-Acetyl-3-(δ-carbomethoxyvaleryl)-digoxigenin

δ-Carbomethoxyvaleryl chloride (1g) was added to a stirred solution of 12-acetyldigoxigenin (2.16 g prepared in the same manner as given for succinyl-digoxigenin-L-tyrosine) in pyridine (~15 ml) under nitrogen atmosphere. The reaction mixture was allowed to stand at room temperature for three hours and was taken up with ethyl acetate and washed with 1N HCl, saturated NaHCO$_3$ and finally with water. The ethyl acetate solution was dried over anhydrous MgSO$_4$ and the solvent was removed under reduced pressure. Purification of the residue by preparative tlc (R$_f$ = 0.206–0.135, acetone-hexane, 7:12) afforded 1.76 g of the desired product, m.p. 66°–70° C.

b. 3-Hemiadipyl Digoxigenin

A mixture of 1.57 g of 12-acetyl-3-(δ-carbomethoxyvaleryl)-digoxigenin, 6 g of potassium carbonate and about 20 ml of methanol was stirred at room temperature for three hours. The methanol was removed at room temperature under reduced pressure and the aqueous solution was diluted with water, washed with ethyl acetate, acidified with cold hydrochloric acid and extracted with three portions of ethyl acetate. The combined extracts were washed with water, dried over magnesium sulfate and stripped of solvent. Purification of the residue by preparative tlc (R$_f$ 0.102–0.17, acetone-hexane, 1:1) gave 0.57 g of the desired acid, m.p. 75° – 95° C.

c. 3-Adipyl-digoxigenin-L-tyrosine methyl ester

A mixture of 323 mg of 3-hemiadipyl digoxigenin, 280 mg of L-tyrosine methyl ester, 210 mg of dicyclohexylcarbodiimide, 5 ml of dioxane and 10 ml of dichloromethane was stirred at room temperature overnight. The urea formed in the reaction mixture was removed by filtratio and the filtrate was diluted with dichloromethane, washed with aqueous sodium bicarbonate, dil. hydrochloric acid, water, dried over magnesium sulfate and concentrated. Purification of the residue by preparative tlc (R$_f$ = 0.06–0.11, acetone-hexane, 10:9) gave 81.1 mg of desired compound, m.p. 80° – 104° C.

d. Preparation of 3-adipyl-digoxigenin-L-tyrosine

A solution of 120 mg 3-adipyl-digoxigenin-L-tyrosine methyl ester in 35 ml of methanol-water (1:1) containingl 70 mg of potassium carbonate was allowed to stand at RT. After 2.5 hours, the methanol was evaporated at RT under reduced pressure and the aqueous solution was acidified with 1N at 0° C. then extracted with three portions of ethyl acetate. The combined extracts were washed with water, dried (MgSO$_4$) and evaporated. Purification of the residue by silica gel preparative tlc (R$_f$ 0.35–0.415, CHCl$_3$-CH$_3$OH-AcOH, 90:10:5) afforded about 129 mg of the desired product, melting point 117°–127° C.

e. Iodination 2 mg of 3-adipyl-digoxigenin-L-tyrosine was iodinated in the same manner as given for 3-succinyl-digoxigenin-L-tyrosine.

3-carbodigoxigenin-glycyl-L-tyrosine I-125

This compound was prepared according to the following sequence and then labelled.

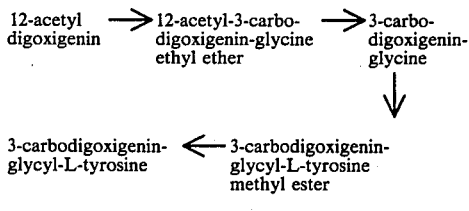

a. 12-Acetyl-3-carbodigoxigenin-glycine ethyl ester

A solution of 4 g of 12-acetyldigoxigenin prepared in the same manner as given for the succinyl derivative, 10 g of ethyl isocyanoacetate in 18 ml of dry pyridine was refluxed with stirring under anhydrous conditions for 5 hours. The pyridine was distilled off and the residue was taken up with ethyl acetate, washed with 1N HCl, water, dried (MgSO$_4$) and stripped of the solvent. The residue was purified by preparative tlc (R$_f$ = 0.30–0.38, acetone-hexane, (1:1) to give 5.96 g of the desired product, melting point 81°–93° C.

b. 3-Carbodigoxigenin-glycine

A solution of 5.06 g of 3-carbodigoxigenin-glycine ethyl ester and 7.5 g of potassium carbonate in 360 ml of methanol-water (1:1) was allowed to stand at RT (room temperature). After 3 hours, the methanol was evaporated off and the aqueous solution ws diluted with water, washed with ethyl acetate, acidified with cold dil. HCl and then extracted with three portions of ethyl acetate. The combined extracts were washed with water, dried (MgSO$_4$) and concentrated to a small volume. The desired product (970 mg, melting point 233–236) precipitated out, was collected by filtration, washed with cold ethyl acetate and dried in vacuum desiccator.

c. 3-Carbodigoxigenin-glycyl-L-tyrosine methyl ester

A solution of 960 mg of 3-carbodigoxigenin-glycine, 960 mg of tyrosine methyl ester and 960 mg of dicyclohexylcarbodiimide in 960 ml of dichloromethane-dioxane (1:1) was stirred at RT overnight. It was filtered to remove the urea formed in the solution and the filtrate was diluted with ethyl acetate, washed in 1N HCl, saturated sodium bicarbonate solution, water, dried (MgSO$_4$). Purification of the residue by preparative tlc ($R_f$ = 0.185-0.318, acetone-hexane-acetic acid-methanol 25:25:1:2) gave 530 mg of the desired product melting point 108°-122°.

d. 3-Carbodigoxigenin-glycyl-L-tyrosine

A solution of 440 mg of 3-carbodigoxigenin-glycyl-L-tyrosine methyl ester and 1.24 g of potassium carbonate in 65 ml of methanol-water (1:1) was allowed to stand at RT. After 3 hours, the methanol was evaporated off and the aqueous solution was acidified with dil. hydrochloric acid at 0° C. and then extracted with three portions of ethyl acetate. The combined extracts were washed with water, dried ($MgSO_4$) and concentrated to a small volume. The crude product precipitated out in the solution was collected (~130 mg) by filtration, washed with cold ethyl acetate and dried in vacuum at boiling temperature of ethyl acetate. The crude product was purified by preparative tlc using $MeOH-CH_2Cl_2$ (2:3) as developing solvent. The band at $R_f$ 0.234-0.420 was scraped from the plate, ground and extracted with methanol. Evaporation of the methanol from the extract gave 106 mg of the product, melting point 220-228 (decomp), which ir showed to be the salt of the desired product. The free acid was prepared by the following manner: A solution of 106 mg of the salt in ~ 3 ml of methanol was acidified with dil. hydrochloric acid at 0° C. and then extracted with 125 ml of ethyl acetate. The ethyl acetate solution was washed with water, dried ($MgSO_4$) and stripped of the solvent to yield 89 mg of 3-carbodigoxigenin-glycyl-L-tyrosine, melting point 150°-158°.

e. Iodination 2 mg of 3-carbodigoxigenin-glycyl-L-tyrosine was iodinated in the same manner as given for 3-succinyl-digoxigenin-L-tyrosine.

PREPARATION OF ANTISERUM

This serum is produced in goats by the monthly injection of 7.5 mg of BSA-Digoxin conjugate emulsified in complete Freunds adjuvant. The conjugate is prepared by periodate oxidation according to Butler and Chen, Biochem J. 1970. Twenty mg are dissolved in one ml of phosphate buffer solution which is added dropwise with rapid mixing through a 1.0 ml tuberculin syringe to an equal volume of complete adjuvant. The material is injected into multiple subcutaneous sites.

The BSA has an E 280 0.1% = 0.67 in 0.01 M phosphate buffer solution.

2.6 ml vials containing dilutions of 1:25,000-1:75,000 are prepared by adding to the vial the following:
1. 0.0000867 ml of antisera
2. 2.6 mg of Bovine Serum Albumin (1:30,000)
3. 0.624 mg of monosodium phosphate monohydrate.
4. 3.61 mg of dibasic potassium phosphate.
5. 22.23 mg of sodium chloride
6. 0.26 mg of $NaN_3$
7. Sufficient water for injection to = 2.6 ml The final dilutions are such that they insure binding eq 60 ± 5% of 3-0-succinyl digoxigenin-L-tyrosine* and displacement by non-radioactive digoxin.

PREPARATION OF DIGOXIN STANDARDS

These are produced by drying U.S.P. Reference Digoxin sample at 105° C. for one hour in a vacuum dessicator, then weighing out 10.0 ± 0.05 mg on an analytical balance. This is quantitatively transferred to a 100 ml volumetric flask and brought to that volume with reagent alcohol at 25 ± 0.5° C. After all the material is in solution and well mixed, one ml is removed with a volumetric pipette and transferred to another 100 ml volumetric flask. The one ml is diluted to 20.0 ml with reagent alcohol and completely mixed. This 20.0 ml is diluted to 100 ml with distilled water. One ml of the 1:100 dilution is then transferred to a 50 ml volumetric flask and diluted to 50 mls with digoxin free normal human serum containing 0.1% $NaN_3$. The product contains 10.0 ng/ml of digoxin (see Part I below). This is diluted with normal human serum containing 0.1% $NaN_3$ (see Part II) to form the various standards and controls solutions.

A typical batch totaling 250 ml consists of two parts each containing

Part I
1. 500 ng digoxin
2. 50 mg $NaN_3$.
3. 0.5 ml Reagent Alcohol
4. $Q_s$ to 50 ml with Normal Human Serum Part II
1. 200 mgs $NaN_3$
2. $Q_s$ to 200 ml with Normal Human Serum The standards are made by diluting part I with Part II as follows:

| Std. ng/ml | ml of Part I | ml of Part II | Dilution Factor | Total Volume mls |
|---|---|---|---|---|
| 0 | 0 | 40.0 | na | 40.0 |
| .4 | 1.0 | 24.0 | 1:25 | 25.0 |
| 1.0 | 2.5 | 22.5 | 1:10 | 25.0 |
| 2.0 | 5.0 | 20.0 | 1:5 | 25.0 |
| 3.0 | 8.0 | 18.6 | 1:3.33 | 26.6 |
| 5.0 | 12.5 | 12.5 | 1:2 | 25.0 |
| Control Sera ng/ml | | | | |
| I 0.6 | 1.5 | 23.55 | 1:16.7 | 25.05 |
| II 1.5 | 4.0 | 22.64 | 1:6.66 | 26.64 |
| III 4.0 | 10 | 15.0 | 1:2.5 | 25.0 |

PREPARATION OF DIGITOXIN STANDARDS

These are produced by drying U.S.P. Reference Digitoxin at 100° C. for 2 hours in a vacuum desiccator. 50 mg is quantitatively transferred to a 100 ml volumetric flask and brought to that volume with methyl alcohol at 25° C. After mixing, 1 ml is transferred to another 100 ml volumetric flask and diluted to 10 ml with methyl alcohol. This 10 ml is diluted to 100 ml with distilled water. 1 ml is transferred to a 50 ml volumetric flask and diluted to 50 ml with digitoxin free normal human serum containing 0.1% $NaN_3$. The product contains 100 ng/ml of digitoxin. This is diluted with normal human serum containing to 0.1% $NaN_3$ to form a 4, 10, 20, 30, 50 and 100 ng/ml standard.

PREPARATION OF KIT COMPONENTS AND KIT

A. Reaction vials: To 99 parts phosphate buffer solution add 1 part of reagent alcohol containing 7-100 nCi/10 ul of 3-0-succinyl digoxigenin tyrosine. Mix mechanically for 1 minute and transfer to an automatic pipette or dispensing device. 1 ml of the above prepared combination reagent is transferred to each reaction vial and the vials are stored at −20° C. (or lower).

B. Digoxin standards prepared as described above.

C. Digoxin, antiserum diluted as described above to contain the dilution of antibody binding 60% of a 7-100 nc quantity of 3-0-succinyl digoxigenin tyrosine 125-I.

D. Ion-exchange resin strips.

A typical packaged test kit contains the following components:
1. 150 reaction vials containing 1 ml. each of the reagent.
2. Bottles containing digoxin standards diluted in digoxin free human serum — 1.5 ml each of the 0, 0.4, 1.0, 2.0, 3.0 and 5.0, ng/ml digoxin standards.
3. Antiserum — 3 bottles containing 2.6 ml each, prediluted.
4. 3 containers, each with 50 ion-exchange resin strips in saline solution.

Components 1,2 and 3 are stored and shipped in the frozen state. Component 4 is not allowed to be frozen and may be stored at room temperature.

RADIOIMMUNOASSAY TEST METHOD

The following procedure is employed in carrying out the radioimmunoassay method of the invention to prepare a standard curve.

1. The required number of reaction vials is removed from the freezer and the net precount per minute is determined for each vial during or after thawing. The thawed reaction vials are gently agitated. Preferably, the test is carried out in triplicate.
2. 50 microliters each of the 0, 0.4, 1.0, 2.0, 3.0 and 5.0 ng/ml standard is added to 18 reaction vials.
3. 50 microliters of antiserum is added to each of the reaction vials and the caps replaced.
4. The vial contents are mixed by rotating for one minute on a rotator at 12–14 rpm or by gently agitating the vial rack.
5. The reaction vials are incubated at room temperature for 30 minutes ± 5 minutes.
6. One ion-exchange resin strip is inserted in each reaction vial and the caps replaced.
7. The reaction vials are rotated for 30 minutes at ambient temperature (20° C. to 30° C.) on a rotator which produces end-over-end mixing at 12–14 rpm.
8. The resin strips are carefully removed and discarded. The resin strips should be allowed to drain over the vials by touching the strip lightly on top of the vial prior to replacing the vial caps.
9. The net postcount per minute is determined for each reaction vial.
10. The % I-125 bound is calculated by dividing the net CPM postcount by the net CPM precount and multiplying by 100.

$$\frac{\text{Net CPM Postcount}}{\text{Net CPM Precount}} \times 100 = \% \text{ I-125 bound to antibody}$$

11. The values obtained should range from 60 + 5% at the 0 ng/ml concentration of digoxin/ml of serum to 20 ± 5% at 10 ng/ml.

The above procedure was followed for 3-succinyl-digoxigenin-L-tyrosin, 3-adipyl-digoxigenin-L-tryosine and 3-carbodigoxigenin-glycyl-L-tyrosine. Results are also given for a control to which no antisera was added.

| 3-succinyl-digoxigenin-L-tyrosine | | | | |
|---|---|---|---|---|
| Concentration of standard ng/ml | Precount CPM | Postcount CPM | % bound | Mean % bound |
| 0 | 11,375 | 7,643 | 67.2 | |
|  | 11,345 | 7,425 | 65.4 | 66.8 |
|  | 11,171 | 7,563 | 67.7 | |
| .4 | 11,297 | 6,700 | 59.3 | |
|  | 11,492 | 6,579 | 57.2 | 58.5 |
|  | 11,287 | 6,658 | 59.0 | |
|  | 11,163 | 5,423 | 48.6 | |
| 1.0 | 11,346 | 5,645 | 49.8 | 49.0 |
|  | 11,349 | 5.512 | 48.6 | |
|  | 11,256 | 3,935 | 35.0 | |
| 2.0 | 11,287 | 3,909 | 34.6 | 35.5 |
|  | 11,206 | 4,140 | 36.9 | |
|  | 11,448 | 3,137 | 27.4 | |
| 3.0 | 11,344 | 3,024 | 26.7 | 27.2 |
|  | 11,203 | 3,080 | 27.5 | |
|  | 11,665 | 2,316 | 19.9 | |
| 5.0 | 11,526 | 2,221 | 19.3 | 19.6 |
|  | 11,410 | 2,242 | 19.6 | |
| Control no Antibody | 11,345 | 645 | 5.7 | |
|  | 11,313 | 674 | 6.0 | 5.5 |
|  | 11,191 | 521 | 4.7 | |

| 3-adipyl-digoxigenin-L-tyrosine | | | | |
|---|---|---|---|---|
| Concentration of standard ng/ml | Precount CPM | Postcount CPM | % bound | Mean % bound |
| 0 | 15,083 | 10,021 | 66.4 | |
|  | 15,513 | 10,050 | 64.8 | 65.2 |
|  | 15,438 | 9,933 | 64.3 | |
| .4 | 15,368 | 8,889 | 57.8 | |
|  | 15,363 | 8.815 | 57.4 | 57.5 |
|  | 15,471 | 8,845 | 57.2 | |
| 1.0 | 15,185 | 6,997 | 46.1 | |
|  | 15,187 | 7.145 | 47.0 | 46.8 |
|  | 15,179 | 7,180 | 47.3 | |
| 2.0 | 15,173 | 5.284 | 34.8 | |
|  | 15,516 | 4,999 | 32.2 | 33.4 |
|  | 15,470 | 5,144 | 33.3 | |
| 3.0 | 15,260 | 3,978 | 26.1 | |
|  | 15,469 | 3,880 | 25.1 | 25.4 |
|  | 15,385 | 3,852 | 25.0 | |
| 5.0 | 15,567 | 2,631 | 16.9 | |
|  | 15,773 | 2,604 | 16.5 | 17.2 |
|  | 15,288 | 2,759 | 18.0 | |
| Control no Antibody | 15,570 | 616 | 4.0 | |
|  | 15,199 | 607 | 4.0 | 3.9 |
|  | 15,647 | 565 | 3.6 | |

| 3-carbodigoxigenin-glycyl-L-tyrosine | | | | |
|---|---|---|---|---|
| Concentration of standard ng/ml | Precount CPM | Postcount CPM | % bound | Mean % bound |
| 0 | 13,733 | 7,833 | 57.0 | |
|  | 13,239 | 7,382 | 55.8 | 56.6 |
|  | 13,648 | 7,769 | 56.9 | |
| 0.4 | 13,348 | 6,786 | 50.8 | |
|  | 13,379 | 6.876 | 51.4 | 51.3 |
|  | 13,337 | 6,907 | 51.8 | |
| 1.0 | 13,370 | 5,273 | 39.4 | |
|  | 13,634 | 5,681 | 41.7 | 41.3 |
|  | 13,830 | 5,936 | 42.9 | |
| 2.0 | 13,830 | 4,363 | 31.5 | |
|  | 13,715 | 4,354 | 31.7 | 31.6 |
|  | 13,371 | 4,202 | 31.4 | |
| 3.0 | 13,980 | 3,571 | 25.5 | |
|  | 13,711 | 3,196 | 23.3 | 25.3 |
|  | 13,641 | 3,670 | 26.9 | |
| 5.0 | 13,804 | 2,526 | 18.3 | |
|  | 13,718 | 2,497 | 18.2 | 17.9 |
|  | 13,934 | 2,379 | 17.1 | |
| Control no Antibody | 13,491 | 739 | 5.5 | |
|  | 14,074 | 761 | 5.4 | 5.2 |
|  | 13,795 | 669 | 4.8 | |

Essentially the same procedure was followed for 3-succinyl-digitoxigenin-L-tyrosine except 25 microliters of each digitoxin standard was used. Results are given below.

| 3-succinyl digitoxigenin-L-tyrosine | | | | |
|---|---|---|---|---|
| Concentration of standard ng/ml | Precount CPM | Postcount CPM | % bound | Mean % bound |
| 0.0 | 16,301 | 11,533 | 70.8 | |
|  | 16,240 | 11,483 | 70.7 | 70.2 |
|  | 16,574 | 11,437 | 69.0 | |
| 4.0 | 16,780 | 11,297 | 67.3 | |
|  | 16,794 | 11,357 | 67.6 | 67.3 |
|  | 16,197 | 10,834 | 66.9 | |
| 10.0 | 16,811 | 10,075 | 59.9 | |
|  | 16,728 | 10,062 | 60.2 | 59.9 |
|  | 16,820 | 10,014 | 59.5 | |

-continued

| 3-succinyl digitoxigenin-L-tyrosine | | | | |
|---|---|---|---|---|
| Concentration of standard ng/ml | Precount CPM | Postcount CPM | % bound | Mean % bound |
| | 16,402 | 7,517 | 45.8 | |
| 20.0 | 16,387 | 7,750 | 47.3 | 46.8 |
| | 16,805 | 7,924 | 47.2 | |
| | 16,104 | 5,465 | 33.9 | |
| 30.0 | 16,888 | 6,193 | 36.7 | 35.6 |
| | 16,335 | 5,911 | 36.2 | |
| | 16,339 | 4,335 | 26.5 | |
| 50.0 | 16,332 | 4,796 | 29.4 | 27.7 |
| | 16,849 | 4,565 | 27.1 | |
| | 17,297 | 3,848 | 22.2 | |
| 100.0 | 16,844 | 3,782 | 22.5 | 22.9 |
| | 16,869 | 4,048 | 24.0 | |
| Control | 16,812 | 3,028 | 18.0 | |
| no | 16,331 | 3,089 | 18.9 | 18.8 |
| Antibody | 16,850 | 3,269 | 19.4 | |

From this data a standard curve can be plotted on semilog graph paper. (% 1–125-linear axis; concentration of standards ng/ml-vertical axis). If a patient's blood serum was also processed, his concentration of total circulting digoxin or digitoxin could be determined from the curve.

As various changes could be made in the above methods and products without departing from the scope of the invention, it is intended that all matter contained in the above desciption shall be interpreted as illustrative. It is to be understood therefore that the invention is not limited except as defined by the appended claims.

What is claimed is:

1. A radioimmunoassay method for the in vitro determination of a cardiotonic glycoside selected from the group consisting of digoxin and digitoxin in unextracted blood serum which comprises the steps of
    a. mixing a sample of blood serum whose cardiotonic glycoside content is to be determined with a reagent comprising an aqueous buffer solution containing a radioactive hapten for said glycoside;
    b. adding to the mixure in an amount by volume equal to the amount by volume of the sample of blood serum an antiserum containing antibody capable of immunoreactivity with said glycoside and said hapten;
    c. incubating the resultant mixture at a temperature and for a sufficient period of time to produce substantial equilibration of the antibody bound hapten and unbound hapten;
    d. adding a relatively thin strip of a membrane consisting essentially of an ion-exchange resin to the mixture and maintaining said membrane in contact therewith at a temperature and for a sufficient period of time to separate the unbound hapten; and
    e. determining the relative amounts of antibody bound radioactive hapten and unbound radioactive hapten.

2. A method according to claim 1 wherein said hapten is radioactive I-125 3-succinyl digoxigenin-L-tyrosine, radioactive I-125 3-succinyl digitoxigenin tyrosine, radioactive I-125 3-adipyl digoxigenin tyrosine, radioactive I-125 3-adipyl digitoxigenin tyrosine, radioactive I-125 3-carbodigoxigenin-glycyl-L-tyrosine, or radioactive I-125 3-carbodigitoxigenin-L-tyrosine.

3. A method according to claim 2, wherein said incubation step is carried out at a temperature of 20° to 24° C. for a period of approximately 30 minutes.

4. A method according to claim 3 wherein said mixture is maintained in contact with said membrane for a period of approximately 30 to 60 minutes at room temperature.

5. A method according to claim 4 wherein said cardiotonic glycoside to be determined is digoxin and said radioactive hapten is radioactive I-125 3-adipyl digoxigen tyrosine.

6. A radioimmunoassay method for the in vitro determination of digoxin in unextracted blood serum which comprises the steps of
    a. mixing a sample of blood serum whose digoxin content is to be determined with a reagent comprising an aqeuous buffer solution containing the radioactive I-125 3-adipyl digoxigenin tyrosine hapten;
    b. mixing with said reagent a digitoxigenin standard containing a known quantity of digoxin in serum, provided that the amount by volume of said digoxin standard mixed with said reagent is equal to the amount by volume of the sample of blood serum.
    1 c. adding to each of the mixtures in an amount by volume equal to the amount by volume of the sample of blood serum an antiserum containing antibody capable of immuno reactivity with said digoxin and said hapten;
    d. incubating the resultant mixtures at approximately room temperature for a period of about 20 to 35 minutes to produce substantial equilibration of the anitbody bound hapten and unbound hapten;
    e. adding a relatively thin strip of a membrane consisting essentially of an ion exchange resin to each of the mixtures and maintaining said membrane in contact therewith at approximately room temperature for a period of 30 to 60 minutes to separate the unbound hapten from the antibody bound hapten; and
    f. determining the relative amounts of antibody bound radioactive hapten and unbound radioactive hapten.

* * * * *